United States Patent [19]

Bigge et al.

[11] Patent Number: 5,968,928

[45] Date of Patent: Oct. 19, 1999

[54] EXCITATORY AMINO ACID ANTAGONISTS: FUSED-AZACYCLIC QUINOXALINEDIONES AND IMMUNOASSAYS THEREOF

[75] Inventors: Christopher Franklin Bigge; Gerald David Nordblom, both of Ann Arbor; Chung Stephen Yi, Lansing, all of Mich.

[73] Assignee: Warner-Lambert Company, Morris Plains, N.J.

[21] Appl. No.: 08/909,471

[22] Filed: Aug. 11, 1997

Related U.S. Application Data

[60] Provisional application No. 60/026,935, Sep. 19, 1996.

[51] Int. Cl.$^6$ ....................... A61K 31/495; A61K 31/55; C07D 487/14
[52] U.S. Cl. .................... 514/215; 544/345; 540/578; 514/250; 435/7.4; 436/545; 436/815
[58] Field of Search ............................ 544/345; 514/250, 514/215; 540/578

[56] References Cited

U.S. PATENT DOCUMENTS

| | | | |
|---|---|---|---|
| 4,889,855 | 12/1989 | Jacobsen et al. | 514/250 |
| 5,081,123 | 1/1992 | Honoré et al. | 514/250 |
| 5,308,845 | 5/1994 | Honoré et al. | 514/250 |
| 5,843,945 | 12/1998 | Watjen et al. | 514/250 |

FOREIGN PATENT DOCUMENTS 0488959  6/1992  European Pat. Off. .

OTHER PUBLICATIONS

C.F. Bigge, and T.C. Malone, "Agonists, Antagonists and Modulators of the N–methyl–D–aspartic acid (NMDA) and α–amino–3–hydroxy–5–isoxazolepropanoic acid (AMPA) Subtypes of Glutamate Receptors", *Current Opinion in Therapeutic Patents*, 1993, pp. 951–989.

M. Rogawski, "Therapeutic potential of excitatory amino acid antagonists: channel blockers and 2,3–benzodiazepines", *TiPS*, vol. 14, 1993, pp. 325–331.

H. Li and A.M. Buchan, "Treatment with an AMPA Antagonists 12 Hours Following Severe Normothermic Forebrain Ischemia Prevents CA$_1$ Neuronal Injury", *Journal of Cerebral Blood Flow and Metabolism*, vol. 13, No. 6, 1993, pp. 933–939.

B. Nellgard and T. Wieloch, "Postischemic Blockade of AMPA but not NMDA Receptors Mitigates Neuronal Damage in the Rat Brain Following Transient Severe Cerebral Ischemia", *Journal of Cerebral Blood Flow and Metabolism*, vol. 12, No. 1, 1992, pp. 2–11.

R. Bullock et al., "Neuroprotective Effect of the AMPA Receptor Antagonists LY–293558 in Focal Cerebral Ischemia", *Journal of Cerebral Blood Flow and Metabolism*, vol. 14, No. 3, 1994, pp. 466–471.

D. Xue et al., "Delayed Treatment with AMPA, but Not NMDA, Antagonsists Reduces Neocortical Infarction", *Journal of Cerebral Blood Flow and Metabolism*, vol. 14, No. 2, 1994, pp. 251–261.

X.–J. Xu et al., "Systemic Excitatory Amino Acid Receptor Antagonists of the α–amino–3–hydroxy–5–methyl–4–isoxazolepropionic acid (AMPA) Receptor and of the N–methyl–D–aspartate (NMDA) Receptor Relieve Mechanical Hypersensitivity After Transient Spinal Cord Ischemia in Rats", *The Journal of Pharmacology and Experimental Therapeutics*, vol. 267, No. 1, 1993, pp. 140–144.

T. Namba et al., "Antiepileptic and anticonvulsant effects of NBQX, a selective AMPA receptor antagonist, in the rat kindling model of epilepsy", *Brain Research*, vol. 638, 1994, pp. 36–44.

S.E. Browne and J. McCulloch, "AMPA receptor antagonists and local cerebral glucose utilization in the rat", *Brain Research*, vol. 641, 1994, pp. 10–20.

S. Yamaguchi et al., "Anticonvulsant activity of AMPA/kainate antagonists: comparison of GYKI 52466 and NBQX in maximal electroshock and chemoconvulsant seizure models", *Epilepsy Research*, vol. 15, 1993, pp. 179–184.

S. Smith et al., "The non–N–methyl–D–aspartate receptor antagonists, BYKI 52466 and NBQX are anticonvulsant in two animal models of reflex epilepsy", *European Journal of Pharmacology*, vol. 201, 1991, pp. 179–183.

T. Klockgether et al., "The AMPA Receptor Antagonist NMQX Has Antiparkinsonian Effects in Monoamine–depleted Rats and MPTP–treated Monkeys", *Annals of Neurology*, vol. 30, No. 5, 1991, pp. 717–723.

T. Klockgether et al., "Toward an Understanding of the Role of Glutamate in Experimental Parkinsonism: Agonist–Sensitive Sites in the Basal Ganglia", *Annals of Neurology*, vol. 34, No. 4, 1993, pp. 585–593.

P. Francis et al., "Cortical Pyramidal Neurone Loss May Cause Glutamatergic Hypoactivity and Cognitive Impairment in Alzheimer's Disease: Investigative and Therapeutic Perspectives", *Journal of Neurochemistry*, vol. 60, No. 5, 1993, pp. 1589–1604.

S. Lipton, "Prospects for clinically tolerated NMDA antagonists: open–channel blockers and alternative redox states of nitric oxide", *TINS*, vol. 16, No. 12, 1993, pp. 527–532.

S. Lipton and P. Rosenberg, "Excitatory Amino Acids as a Final Common Pathway for Neurologic Disorders", Review Article in *Mechanisms of Disease*, F. Epstein, Editor, vol. 380, No. 9, 1993, pp. 613–622.

*Primary Examiner*—Mukund J. Shah
*Assistant Examiner*—Ann M. Kessinger
*Attorney, Agent, or Firm*—Elizabeth M. Anderson

[57] ABSTRACT

The invention discloses novel fused-azacylic quinoxalinediones. These compounds may be employed as excitatory amino acid antagonists and as analogs for use in immunological assays. The invention is also directed to both a radioimmunoassay and enzyme immunoassay for detecting and quantitating 1,4,7,8,9,10,-hexahydro-9-methyl-6-nitropyrido[3,4-f]-quinoxaline-2,3-dione PNQX and analogs thereof.

9 Claims, No Drawings

EXCITATORY AMINO ACID ANTAGONISTS: FUSED-AZACYCLIC QUINOXALINEDIONES AND IMMUNOASSAYS THEREOF

This application claims the benefit of U.S. Provisional application Ser. No. 60/026,935, filed Sep. 19, 1996.

BACKGROUND OF THE INVENTION

1. Field of the Invention

This invention relates to novel fused-azacyclic quinoxalinediones that may be employed as excitatory amino acid antagonists. The invention also relates to both a radioimmunossay and enzyme immunoassay for certain fused-azacyclic quinoxalinediones and novel analogs of fused-azacyclic quinoxalinediones employed in such immunoassays.

2. Related Background Art

Excessive excitation by neurotransmitters can cause the degeneration and death of neurons. It is believed that this degeneration is in part mediated by the excitotoxic actions of the excitatory amino acid (EAA) glutamate and aspartate at the N-methyl-D-aspartate (NMDA), the α-amino-3-hydroxy-5-methyl-4-isoxazole propionate acid (AMPA) receptor, and the kainate receptor. This excitotoxic action is responsible for the loss of neurons in cerebrovascular disorders such as cerebral ischemia or cerebral infarction resulting from a range of conditions, such as thromboembolic or hemorrhagic stroke, cerebral vasospasms, hypoglycemia, cardiac arrest, status epilepticus, perinatal asphyxia, anoxia such as from drowning, pulmonary surgery, and cerebral trauma, as well as lathyrism, Alzheimer's, Parkinson's, and Huntington's disease. Several classes of quinoxalinedione derivatives have been disclosed as glutamate (EAA) receptor antagonists. For example, U.S. Pat. No. 4,889,855, generically discloses compounds of the formulae:

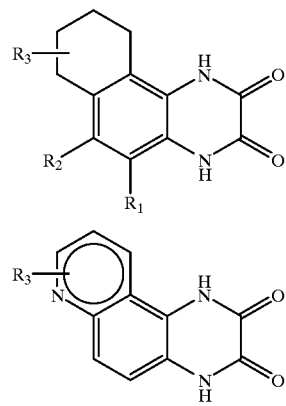

wherein $R_1$, $R_2$ and $R_3$ are independently H, halogen, CN, $NH_2$, $NO_2$, $SO_3H$, $SO_2NH_2$, and $CONH_2$. This reference specifically discloses 6-amino, 6-cyano, 5-carbamoyl, 6-nitro, and 5,6-dinitro-7,8,9,10-tetrahydro-2,3-dihydroxybenzo(f)quinoxalines. The reference, however, does not disclose any compounds with an azacycloalkyl fused ring, let alone an N-substituted ring. Nor does the reference disclose or suggest any methods which would allow the preparation of N-substituted azacycloalkyl ring fused compounds. U.S. Pat. Nos. 5,081,123 and 5,308,845, describe similar structures except that there is respectively a hydroxy or alkoxy function at the nitrogen on the quinoxalinedione skeleton. Again, however, these references do not suggest or illustrate any examples of N-substituted fused azacycloalkyl quinoxalinediones.

Among excitatory amino acid receptor antagonists recognized for usefulness in the treatment of disorders are those that block AMPA receptors (Bigge C. F. and Malone T. C., Curr. Opin. Ther. Pat., 1993;951, Rogawski M. A., TiPS 14, 1993;325). AMPA receptor antagonists have prevented neuronal injury in several models of global cerebral ischemia (Li H. and Buchan A. M., J. Cerebr. Blood Flow Metab., 1994;13:933, Nellgard B. and Wieloch T., J. Cerebr. Blood Flow Metab., 1992;12:2) and focal cerebral ischemica (Bulock R., Graham D. I., Swanson S., McCulloch J., J. Cerebr. Blood Flow Metab., 1994;14:466); Xue D., Huang Z.-G., Barnes K., Lesiuk H. J., Smith K. E., Buchan A. M., J. Cerebr. Blood Flow Metab., 1994;14:251. AMPA antagonists have also shown efficacy in models for analgesia (Xu X.-J., Hao J.-X, Seiger A., Wiesenfeld-Hallin Z., J. Pharmacol. Exp. Ther., 1993;267:140), and epilepsy (Namba T., Morimoto K., Sato K., Yamada N., Kuroda S., Brain Res., 1994;638:36; Brown S. E., McCulloch J., Brain Res., 1994;641:10; Yamaguchi S. I., Donevan S. D., Rogawski M. A., Epilepsy Res., 1993;15:179; Smith S. E., Durmuller N., Meldrum B. S., Eur. J. Pharmacol., 1991;201:179) AMPA receptor antagonists have also demonstrated promise in chronic neurodegenerative disorders such as Parkinsonism. (Klockgether T., Turski L., Honeré T., Zhang Z., Gash D. M., Kurlan R., Greenamyre J. T., Ann. Neurol., 1993;34(4):585–593.)

Excitatory amino acid receptor antagonists that block nmDA receptors are also recognized for usefulness in the treatment of disorders. nmDA receptors are intimately involved in the phenomenon of excitotoxicity, which may be a critical determinant of outcome of several neurological disorders. Disorders known to be responsive to blockade of the nmDA receptor include acute cerebral ischemia (stroke or cerebral trauma, for example), muscular spasm, convulsive disorders, neuropathic pain and anxiety, and may be a significant causal factor in chronic neurodegenerative disorders such as Parkinson's disease (Klockgether T., Turski L., Ann. Neurol. 1993;34:585–5933), human immunodeficiency virus (HIV) related neuronal injury, amyotrophic lateral sclerosis (ALS), Alzheimer's disease (Francis P. T., Sims N. R., Procter A. W., Bowen D. M., Neurochem J. 1993;60(5):1589–1604) and Huntington's disease. (See Lipton S. A., TINS 1993;16(12):527–532; Lipton S. A., Rosenberg P. A., New Eng. J. Med. 1994;330(9):613–622; and Bigge C. F., Biochem. Pharmacol., 1993;45:1547–1561 and references cited therein.) nmDA receptor antagonists may also be used to prevent tolerance to opiate analgesia or to help control withdrawal symptoms from addictive drugs (Eur. Pat. Appl. 488,959A).

Copending U.S. patent application Ser. No. 08/124,770 discloses glutamate receptor antagonist quinoxalinedione derivatives represented by the formula:

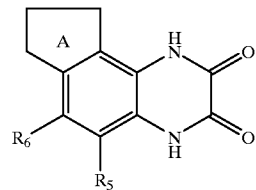

wherein A is a 5 to 7 atom containing ring having a nitrogen which may be substituted by hydrogen, alkyl, or CH₂CH₂OH. This application does not disclose or suggest compounds having different nitrogen substituents, or the requisite methodology to prepare the same.

Copending U.S. patent application Ser. No. 08/404,400 discloses certain N-substituted fused azacycloalkylquinoxalinediones wherein the N-substituent may be selected from alkylCOOR³, alkylamine, alkylguanidine, aryl, alkylaryl, COalkyl, COalkylaryl, CSNR³alkylaryl, or a common amino acid moiety joined by an amine bond and wherein R³ is hydrogen, alkyl, or alkylaryl. However, additional derivatives of N-substituted fused azacycloalkylquinoxalinediones that are useful as excitory amino acid antagonists would be desirable. It is also highly desirable to have an accurate manner of assaying N-substituted fused azacycloalkylquinoxalinediones in plasma and in cerebrospinal fluid or brain microdialysate to assist in the study of these compounds in their use as neuroprotective agents.

SUMMARY OF THE INVENTION

This invention relates to a compound represented by the Formula (I):

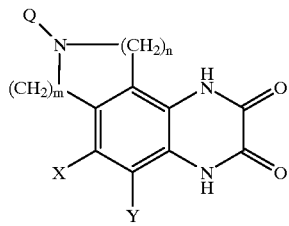

or a pharmaceutically acceptable salt thereof wherein X and Y are independently hydrogen, halogen, nitro, cyano, —CF₃, —COOH, CONR¹R², SONR¹R², COR³, SO₂R³, alkyl, alkenyl, imidazolyl or imidazolidinyl; wherein R¹ and R² are independently hydrogen, alkyl having 1 to 6 carbon atoms, cycloalkyl, aralkyl or join together to form a heterocyclic ring; and wherein R³ is alkyl, haloalkyl, cycloalkyl, aryl or aralkyl; Q is —CO(CH₂)$_p$NR⁴R⁵, —CSNR⁶aryl, —COheterocyclic, —SO₂heterocyclic, —(CH₂)$_r$CO(CH₂)$_p$COOR⁷, —(CH₂)$_r$CONR⁴R⁵, —(CH₂)$_r$CONH(CH₂)$_s$CONR⁴R⁵, —(CH₂)$_r$CONH(CH₂)$_s$COOR⁷, —(CH₂)$_r$CONH(CH₂)$_s$CONHNHCO(CH₂)$_v$NHCOR⁹, —(CH₂)$_r$CONHNHCO(CH₂)$_s$NHCOR⁹, or (CH₂)$_r$CN wherein R⁴, R⁵, R⁶, and R⁷ are independently hydrogen, alkyl having 1 to 6 carbon atoms, aryl having 6 to 20 carbon atoms, aralkyl having 7 to 20 carbon atoms, alkylene COOR⁸ or alkylene heterocyclic any of which may be substituted by one or more alkyl, halo, hydroxy or ¹²⁵I groups, wherein R⁸ is hydrogen, alkyl, aralkyl or aryl, wherein R⁹ is

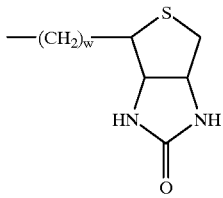

and wherein p, r, s, v and w are independently 1 to 6; and m and n are independently 0, 1 or 2 provided that m+n is >1.

Examples of pharmaceutically acceptable addition salts include inorganic and organic acid addition salts such as the hydrochloride, hydrobromide, phosphate, sulphate, citrate, lactate, tartrate, maleate, fumarate, mandelate, oxalate, and the acetate. Alternatively, pharmaceutically acceptable inorganic and organic base addition slats may be used such as sodium hydroxide, potassium hydroxide, lithium hydroxide, and the like.

Alkyl means a straight chained or branched chain of from 1 to 6 carbon atoms or cyclic alkyl of from 3 to 7 carbon atoms including, but not limited to methyl, ethyl, propyl, isopropyl, butyl, isobutyl, t-butyl, pentyl, hexyl, cyclopropyl, cyclobutyl, cyclopentyl, and cyclohexyl.

Alkenyl means a straight chained or branched chain alkenyl group of 2 to 6 carbon atoms or a cyclic alkenyl group of 3 to 8 carbon atoms, for example, but not limited to ethylene, 1,2- or 2,3-propylene, 1,2-, or 3,4-butylene, cyclopentane, or cyclohexane.

Alkynyl means a straight chained or branched chain alkynyl group of 2 to 6 carbon atoms, for example, but not limited to ethynyl, 2,3-propynyl, 2,3- or 3,4-butynyl.

Alkylene means a divalent group having 1 to 6 methylene units.

Aryl means a monocyclic or bicyclic carbocyclic aromatic ring system, for example, but not limited to phenyl, 2-naphthyl, or 1-naphthyl.

Aralkyl mean aryl as defined above and alkyl as defined above, for example, but not limited to benzyl, 2-phenylethyl, 3-phenylpropyl; a preferred group is benzyl.

Halogen is fluorine, chlorine, bromine, or iodine; fluorine, chlorine and bromine are preferred groups.

The alkyl, alkenyl, alkynyl, alkylene, aryl, and aralkyl may be substituted by one or more alkyl, halo, hydroxy, or ¹²⁵I groups.

Heterocyclic means an aromatic or non-aromatic ring structure having 5 to 6 members in which one or more of the elements in the ring is an element other than carbon, e.g., nitrogen, sulfur, or oxygen.

Typical non-aromatic heterocyclic groups include any of the following which may be optionally substituted with one or more alkyl, halo, hydroxy, or ¹²⁵I groups: tetrahydrofuranyl, pyranyl, piperidinyl, piperazinyl, pyrrolidinyl, imidazolindinyl, imidazolinyl, indolinyl, isoindolinyl, quinuclidinyl, morpholinyl, isochromanyl, chromanyl, pyrazolidinyl, and pyrazolinyl groups.

Typical aromatic heterocyclic (heteroaryl) groups include any one of the following which may be optionally substituted with one or more alkyl, halo, hydroxy or ¹²⁵I groups: thienyl, benzo[b]thienyl, naphtho[2,3-b]thienyl, thianthrenyl, furyl, pyranyl, isobenzofuranyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, β-carbolinyl, phenanthridinyl, acridinyl, permidinyl, phenanthrolinyl, phenazinyl, isothiazolyl, phenothiazinyl, isoxazolyl, furazanyl phenoxazinyl groups, 1,4-dihydroquinoxaline-2,3-dione, 7-amino isocoumarin, pyrido[1,2-a]pyrimidine-4-one, 1,2-benzisoxazole-3-yl, benzimidazolyl, 2-oxobenzimidazolyl, 2-oxindolyl, and 4-nitrobenzofurazan. Where the heteroaryl group contains a nitrogen atom in a ring, such nitrogen atom may be in the form of an N-oxide, e.g., a pyridinyl N-oxide, pyrazinyl N-oxide, pyrimidinyl N-oxide and the like.

The instant invention is also related to a pharmaceutical composition containing the compound defined by Formula I (provided it is not radio labeled) in an amount effective to treat cerebrovascular disorders responsive to the blockade of glutamate receptors, including either or both nmDA receptors and non-NMDA receptors (such as the α-amino-3-hydroxy-5-methyl-4-isoxazole propionic acid (AMPA) receptor and the kainate receptor), and a pharmaceutically acceptable carrier. Exemplary disorders responsive to such treatment include cerebral ischemia caused by cerebral trauma, stroke, hypoglycemia, heart attack, and surgery; anxiety and schizophrenia; and chronic neurodegenerative disorders such as Huntington's disease, ALS, Parkinsonism, and Alzheimer's disease. The pharmaceutical composition of this invention may also be employed as an analgesic or for the treatment of epilepsy.

The invention further relates to a method of treating cerebrovascular disorders responsive to antagonism of glutamate receptors including either or both nmDA receptors and non-NMDA receptors by administering a compound of above-defined Formula I (provided it is not radio labeled) in a unit dosage form.

The invention also relates to a radioimmunoassay and an enzyme immunoassay for detecting 1,4,7,8,9,10-hexahydro-9-methyl-6-nitropyrido[3,4-f]-quinoxaline-2,3-dione and analogs thereof. These assays have been found to be particularly useful for detecting and quantitating such compounds in bodily fluids or tissue, e.g. plasma or brain interstitial fluid.

DETAILED DESCRIPTION OF THE INVENTION

The fused-azacyclic quinoxalinediones of this invention are represented by previously defined Formula I. Such compounds may be employed as excitatory amino acid antagonists or as components of the radioimmunoassay and enzyme immunoassay techniques for detecting and quantitating 1,4,7,8,9,10-hexahydro-9-methyl-6-nitropyrido[3,4-f]-quinoxaline-2,3-dione [PNQX] and analogs thereof.

Preferably, X and Y of Formula I are independently hydrogen, bromo, and nitro. It is also preferred that the azacyclic ring is a five or six membered ring.

Particularly preferred compounds of the present invention include, without limitation:
  9-Diethylaminoacetyl-6-nitro-1,4,7,8,9,10-hexahydro-pyrido[3,4-f]quinoxaline-2,3-dione;
  9-(4-Dimethylamino-butyryl)-6-nitro-1,4,7,8,9,10-hexahydro-pyrido[3,4-f]quinoxaline-2,3-dione;
  9-(3-Diethylamino-propionyl)-6-nitro-1,4,7,8,9,10-hexahydro-pyrido[3,4-f]quinoxaline-2,3-dione;
  6-Nitro-2,3-dioxo-1,2,3,4,7,10-hexahydro-8H-pyrido[3,4-f]quinoxaline-9-carbothioic acid phenylamide;
  6-Nitro-9-[2-(2H-tetrazol-5-yl)-benzoyl]-1,4,7,8,9,10-hexahydro-pyrido[3,4-f]quinoxaline-2,3-dione;
  6-Nitro-9-(thiophene-2-sulfonyl)-1,4,7,8,9,10-hexahydro-pyrido[3,4-f]quinoxaline-2,3-dione;
  9-(1-Methyl-1H-imidazole-4-sulfonyl)-6-nitro-1,4,7,8,9,10-hexahydro-pyrido[3,4-f]quinoxaline-2,3-dione;
  4-[2-(6-Nitro-2,3-dioxo-1,2,3,4,7,10-hexahydro-8H-pyrido[3,4-f]quinoxaline-9yl)-acetylamino]-butyric acid methyl ester;
  2-(6-Nitro-2,3-dioxo-1,2,3,4,7,10-hexahydro-8H-pyrido[3,4-f]quinoxaline-9-yl)-N-phenethyl-acetamide;
  4-(6-Nitro-2,3-dioxo-1,2,3,4,7,10-hexahydro-8H-pyrido[3,4-f]quinoxaline-9-yl)-butyronitrile; and
  4-[2-(6-Nitro-1,2,3-dioxo-1,2,3,4,7,10-hexahydro-8H-pyrido[3,4-f]quinoxaline-9-yl)-acetylamino]-butyric acid.

Particularly preferred compounds for use in the immunoanalytical assays of this invention, include without limitation, those of Formula I wherein Q is —CH$_2$CONHR', and wherein R' is selected from the group consisting of

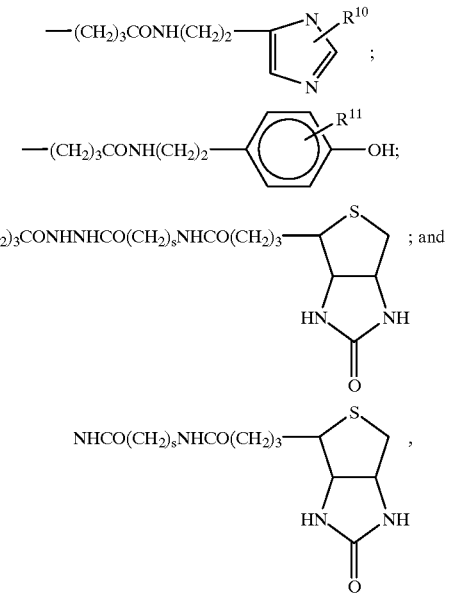

wherein $R^{10}$ and $R^{11}$ are $^{125}$I.

The chemistry used for the preparation of the derivatives described herein utilizes the free amine of the fused azacycloquinoxalinedione as a nucleophile reacting with an electrophile, such as but not limited to, an alkyl halide (tosylate, mesylate, etc.), acyl halide (or other activated carboxylic acid moiety using a reagent such as EDAC, HOBT, HBTU, DCC, CDI, etc.), a sulfonyl chloride (or equivalent), and other electrophiles such as isocyanates or isothiocyanates. Where the terminal functional group is an amine or carboxylic acid, methods known to those skilled in the art may be used to elaborate the side chains to provide the desired final products, including those adducts used for the development of the radioimmunoassay and enzyme immunoassay.

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Tablets containing 10 mg of active ingredients or, more broadly, 0.1 to 100 mg per tablet, are accordingly suitable representative unit dosage forms.

Solid forms of pharmaceutical compositions for PO administration and injectable solutions are preferred.

The compounds of this invention are extremely useful in the treatment of central nervous system disorders related to their biological activity. The compounds of this invention may accordingly be administered to a subject, including a human, in need of treatment, alleviation, or elimination of an indication associated with the biological activity of the compounds. This includes especially excitatory amino-acid-dependent psychosis, excitatory amino-acid-dependent anoxia, excitatory amino-acid-dependent ischemia, excitatory amino-acid-dependent parkinsonism, excitatory amino-acid-dependent convulsions, and excitatory amino-acid-dependent migraine. Suitable dosage ranges are 0.1 to 1000 mg daily, dependent as usual upon the exact mode of administration, the form in which administered, the indication toward which the administration is directed, the subject involved, and the body weight of the subject involved, and further the preference and experience of the physician or veterinarian in charge.

Another embodiment of the present invention is directed to immunoanalytical methods for detecting and measuring 1,4,7,8,9,10-hexahydro-9-methyl-6-nitropyrido[3,4-f]quinoxaline-2,3-dione [PNQX] and analogs thereof in biological fluids and tissue using compounds described in Formula I. The immunoassay could possible be used for any analog of PNQX. However, the preferred compounds for assay include those which have the 6-nitro substituent on the quinoxolinedione moiety.

To conduct the immunoanalytical methods of this invention an antibody to PNQX is obtained using a compound described in Formula I which is conjugated with a large protein such as porcine thyroglobulin bovine serum albumin, keyhole limpet hemocyanin, and the like. The preferred side chain is —(CH$_2$)$_r$ CONH(CH$_2$)$_s$COOR$^7$. An appropriate animal, e.g. New Zealand white rabbits, is immunized to develop the antibody, after which the antisera is collected by venipuncture and prepared by centrifugation. The antisera, and the antibody contained therein, is then used in the immunoanalytical techniques of this invention.

The radioimmunoassay is conducted by mixing (i) an antisera containing the antibody of PNQX and (ii) a radioiodinated or tritiated compound of Formula I with (iii) the biological fluid or extract of tissue to be assayed. The radioiodinated N-tyramine and N-histamine derivatives of Formula I are particularly preferred.

Schemes 1 and 2 below exemplify the preparation of several preferred radioiodinated compounds of Formula I.

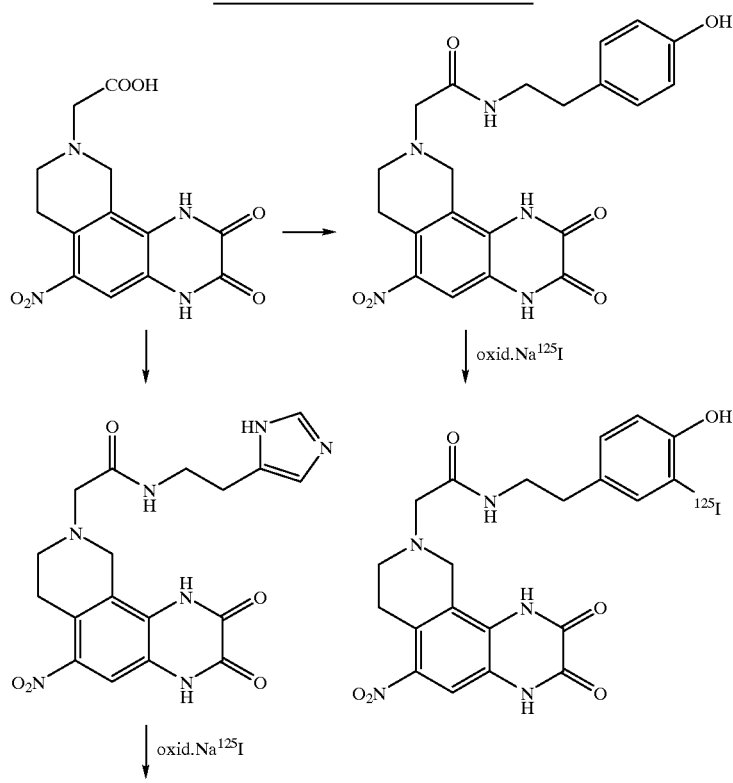

-continued

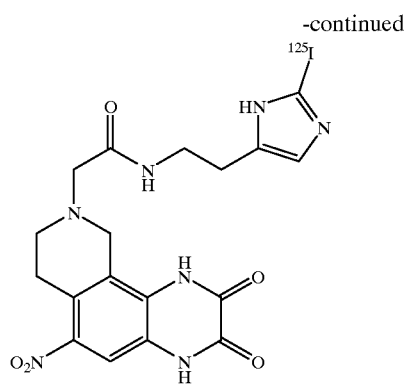

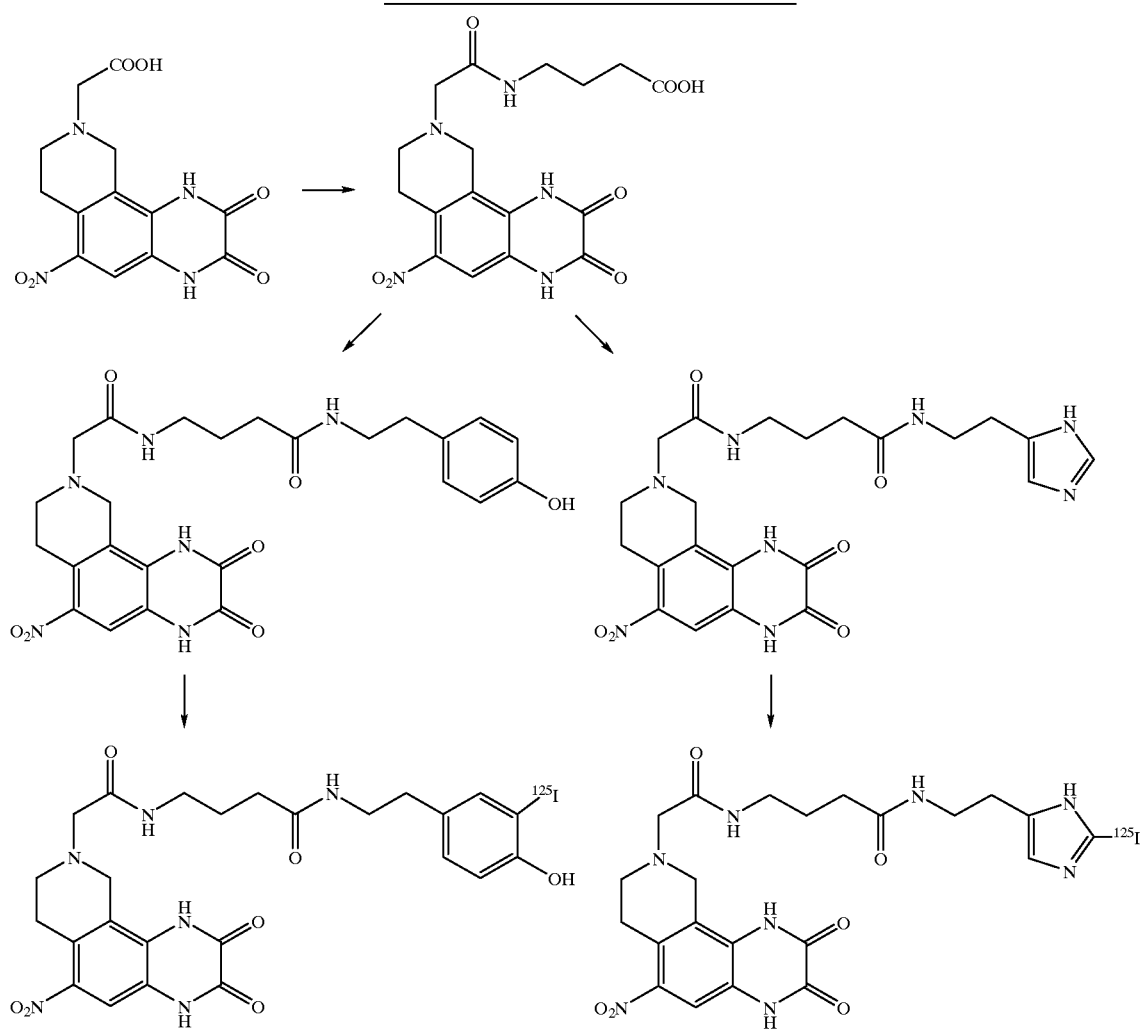

Scheme 2
Long Chain Radiolabel for PNQX Radioimmunoassay

After components (i), (ii), and (iii) have been mixed, they are allowed to set for a period of time, e.g. two hours, at room temperature. A second antibody against primary antibody IgG, e.g., sheep anti-rabbit anti-PNQX analog IgG, is added to precipitate the rabbit anti-PNQX IgG-radiolabeled complex and centrifuged. Unbound radiolabel is removed by decanting or aspiration. The resulting precipitate is measured for radioactivity.

To determine the concentration of PNQX or PNQX analog, standard solutions of specific compound being assayed are analyzed in the manner described above. Thereafter, the percent of radiolabeled compound found is plotted versus concentration to generate a standard curve. The standard curve is then used to obtain a quantitative number for the biological fluids and tissue that are assayed.

The enzymatic immunoassay of this invention for 1,4,7,8,9,10-hexahydro-9-methyl-6-nitropyrido[3,4-f]-quinoxaline-2,3-dione [PNQX] and analogs thereof is conducted using anti-PNQX-IgG obtained from the antisera described above. The anti-PNQX-IgG is adhered to a solid surface, e.g. the surface of wells in a flat bottom Immunlon® 4 disposable microtitration polystyrene plate from Dynatech, Chantily, Va. This plate is 12.8×8.6 cm and has 96, 7 mm×1 cm wells. However, any equivalent polystyrene 96-well plate would be sufficient. If wells are used, the anti-PNQX-IgG is poured into the wells and allowed to sit overnight. The solution is then poured off leaving the antibody physically adhered to the surface of the well.

Next, a biotinylated compound of Formula I and a sample of bodily fluid or tissue are added to the well. This is allowed to incubate from 0.5 to four hours. Then the solution is poured out of the well or whatever solution holding vessel having a solid surface is used.

Schemes 3 and 4 below exemplify the preparation of several biotinylated compounds of Formula I.

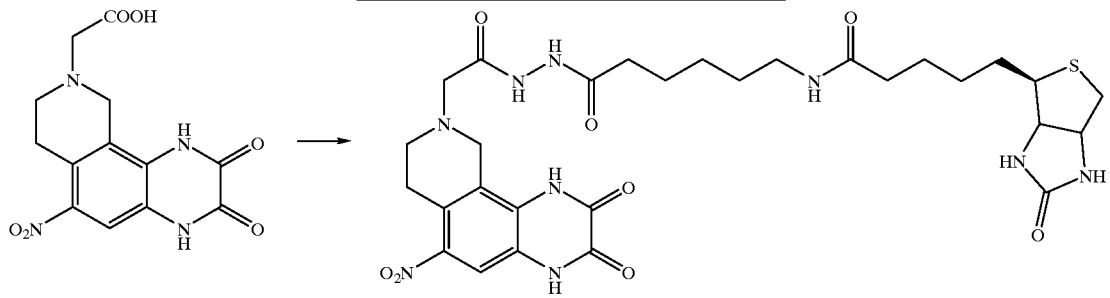

Scheme 3
Biotinylated Derivative for PNQX Enzyme Immunoassay

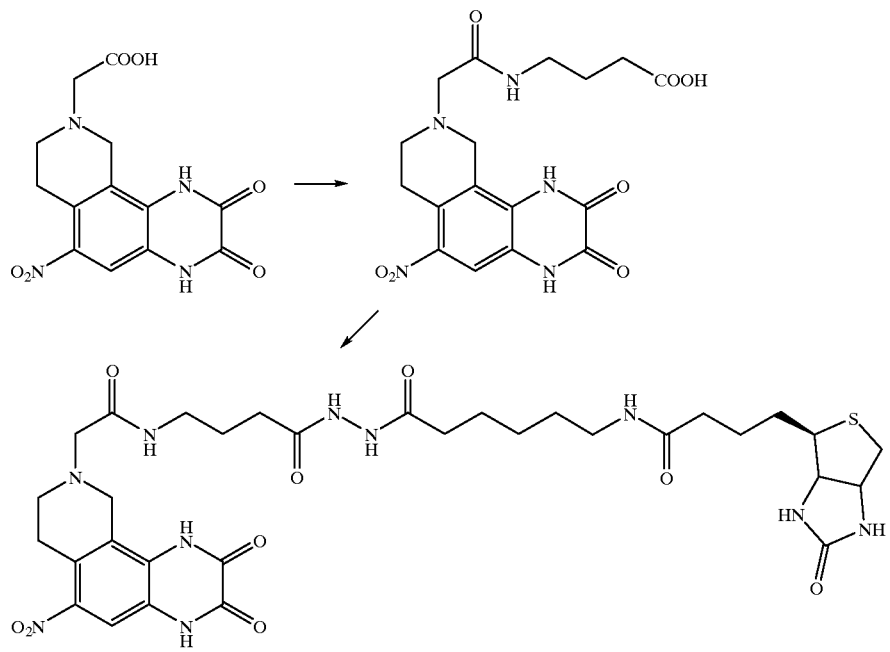

Scheme 4
Long Chain Biotinylated Derivative for PNQX Enzyme Immunoassay

After washing the well, avidin-horseradish peroxidase is added to the solution holding substrate. Due to the high measure of affinity between avidin and biotin the added avidin binds to the biotin compound which is adhered to the anti-PNQX-IgG which in turn is adhered to the surface of the substrate. The excess is washed out and tetramethyl benzidine or other horse radish peroxidase substrate is added. This reacts with the bound avidin enzyme to form a color. The color is then read using a 96-well spectrophotometer (Tecan Instruments, Research Triangle Park, N.C.). Quantitation can be performed by generating a concentration curve in a manner similar to that described above.

The examples which follow are intended as an illustration of certain preferred embodiments of the invention, and no limitation of the invention is implied.

EXAMPLE 1

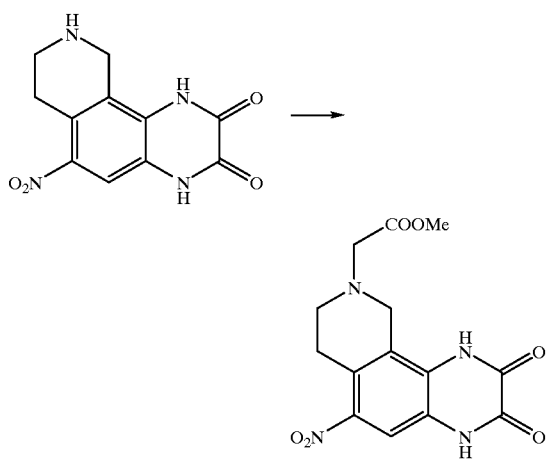

A mixture of the 6-nitro-pyridoquinoxalinedione (260 mg, 1 mmol), diisopropylethyl amine (1.2 mmol), and DMF (5 mL) was stirred while heating in an oil bath at 60° C. for 30 minutes. Methyl bromoacetate (0.11 mL) was added and the reaction proceeded for 3 hours. The mixture was cooled to room temperature and treated with water (50 mL) and allowed to stand overnight. The precipitate was collected by filtration and washed exhaustively with water and then diethyl ether. Drying in vacuo gave a light yellow solid (0.255 gm, 76% yield); mp=260–263° C. (dec), MS m/e M+1 335, $^1$H-NMR, CHN.

EXAMPLE 2

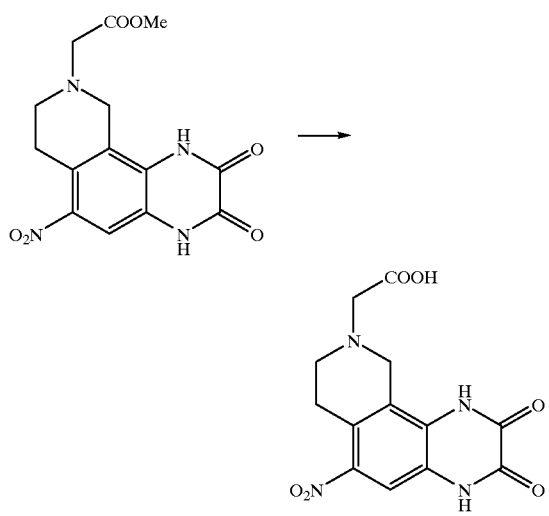

A suspension of the amino acid ester (0.1 g) from Example 1 in THF (5 mL) was stirred and treated portionwise with 1N NaOH solution (1.2 mL) over 3 hours. The reactant clumped, and the mixture was heated in an oil bath at 60° C. for 1 hour, which gave a solution. The mixture was cooled to room temperature an neutralized with 2N HCl. A colloidal mixture resulted. Silica gel was added to the mixture until no liquid remained. The silica gel was placed in a sintered glass funnel and eluted with diethyl ether, and then with methanol. The colored material adsorbed onto the glass and was washed with 4:1 methanol:triethylamine solution and evaporated to give the product as the triethylammonium salt.

Alternatively, after hydrolysis of 0.14 g of the ester, a 1:1 mixture of THF:ether was added to the reaction mixture. The water and organic layers were separated. The water layer, which was a colloidal suspension, was treated with acetone to produce a flocculent solid. The solid was collected by filtration and washed with diethyl ether to give a light yellow solid as the free acid in quantitative yield, MS, nmR.

EXAMPLE 3

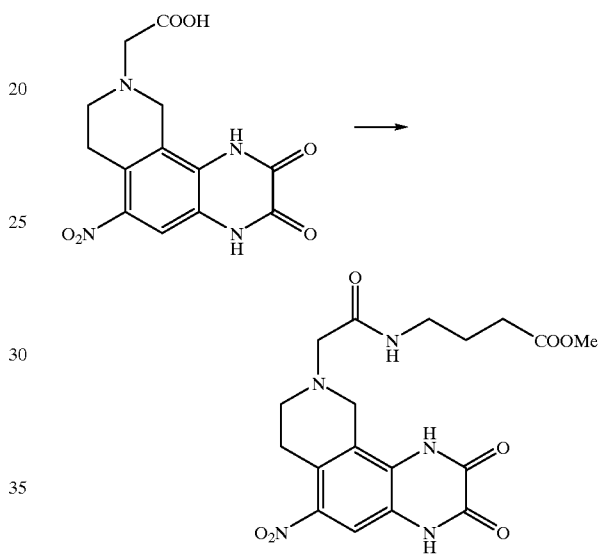

A suspension of the free acid from Example 2 (30 mg, 0.07 mmol) in DMF (2 mL) and acetonitrile (5 mL) was cooled in an ice bath. HBTU (35 mg) and diisopropylethyl amine were added consecutively, and the mixture stirred for 15 minutes at 0° C. A solution of methyl 4-aminobutyrate hydrochloride (24 mg) and diisopropylethyl amine in 1 mL acetonitrile was added and the reaction mixture allowed to warm to room temperature and stir overnight. The reaction mixture was diluted with diethyl ether:THF 1:1 and water. A solid precipitate was collected by filtration and purified using C-18 reverse phase silica gel to give the product (35 mg).

EXAMPLE 4

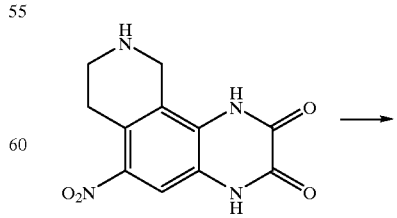

15
-continued

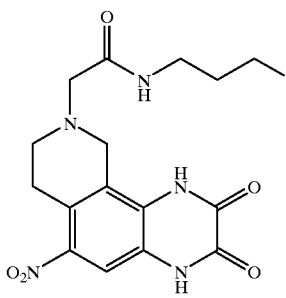

A mixture of the 6-nitro-pyridoquinoxalinedione (0.5 g, 1.9 mmol) in DMF (25 mL) was treated with triethylamine (350 μL) and (methyl-4-aminobutyrate)-bromoacetamide (0.54 g, 2.25 mmol) and heated at 70° C. for 5 hours. The mixture was cooled to room temperature and triturated with water (50 mL). The precipitate was collected by filtration, washed with water, then ether, and dried in vacuo to give an orange solid (0.61 g), mp=153–157° C. (dec); m/e M+1 420, nmR, IR.

16
-continued

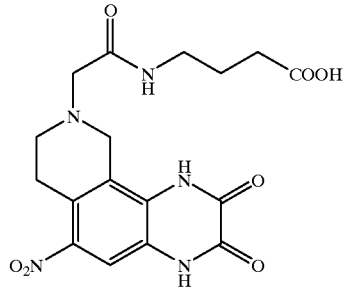

A solution of potassium trimethylsilanolate (0.73 g, 5.7 mmol) in THF (50 mL) was cooled in an ice bath and treated with the methyl ester from Example 4 (0.4 g, 0.95 mmol). After stirring for 4 hours, the solvent was removed and the product dissolved in water and extracted three times with diethyl ether. The water layer was chromatographed on C-18 reverse phase silica gel using 9:1 0.5N formic acid buffer-:acetonitrile. The product precipitated from the column fractions as the free acid.

EXAMPLE 6

Alternatively, the methyl ester from Example 4 (1.9 mmol) was stirred in 1N NaOH (50 mL) for 2 hours. The water was removed in vacuo, and the residue crystallized from 0.5M formic acid, pH 3. The free acid (0.68 g) was obtained after drying as a brown solid; m/e M+1 406.

EXAMPLE 7

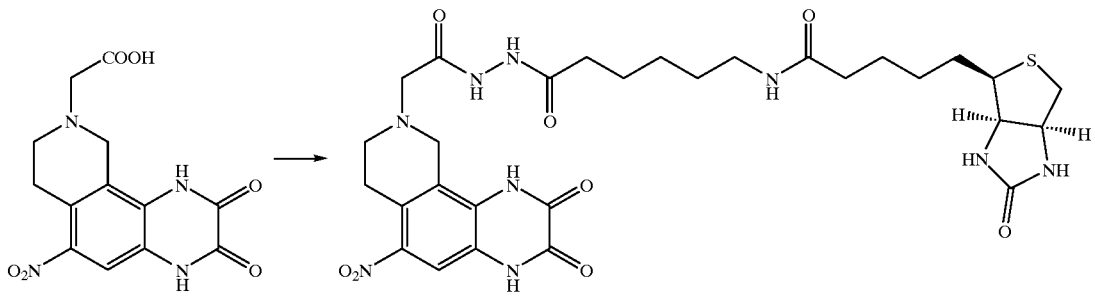

EXAMPLE 5

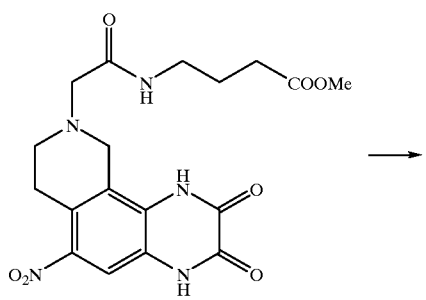

A mixture of the free acid from Example 2 (20 mg, 0.07 mmol) in DMF (3 mL) was stirred in an ice bath and then treated with 2-(1-H-Benzotriazole-1-yl)-1,1,3,3-tetramethyluronium hexafluorophosphate (HBTU) (30 mg, 0.08 mmol), and then diisopropylethyl amine (0.1 mL). After stirring for 30 minutes, biotinyl caproyl hydrazide (Sigma, 30 mg, 0.08 mmol) was added. After stirring overnight, the mixture was treated with acetone, diethyl ether 1;1, and stirred. A precipitate was collected by filtration, washed with acetone:diethyl ether, and then washed with ther. A brown orange solid was obtained (50 mg). The material was purified by C-18 reverse phase chromatography (Alltech 30–70μ, 15 g) using a step gradient of water, 5%, 10%, 15%, 20%, and 50% acetonitrile/water, and then switching to methanol/water gradient to 100% methanol. The fractions were monitored by HPLC, and an enzyme immunoassay was used to identify the product fractions.

EXAMPLE 8

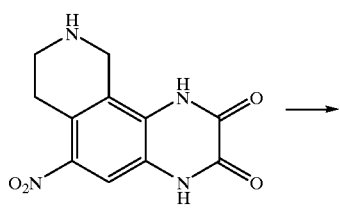

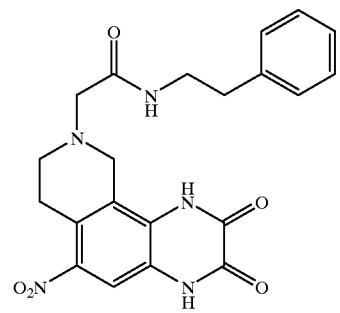

A mixture of the 6-nitro-pyridoquinoxalinedione (0.1 g, 0.38 mmol), and triethylamine 0.06 mL in THF (5 mL) and DMF (5 mL) was treated with (phenylethyl)-bromoacetamide (0.1 g, 0.4 mmol) and heated at 55° C. for 24 hours. Additional bromoacetamide derivative (15 mg) was added, and the reaction continued at 60° C. for 21 hours. The reaction mixture was cooled and treated with water (200 mL). The precipitate was collected by filtration and washed with water and ether and dried in vacuo to give the product (107 mg) in 66% yield. mp=246–250° C.; m/e M+1 424, nmR.

EXAMPLE 9

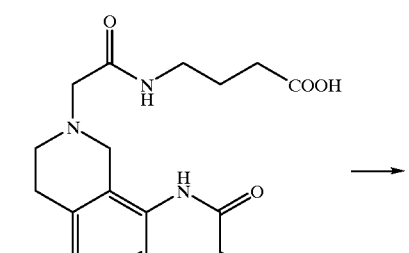

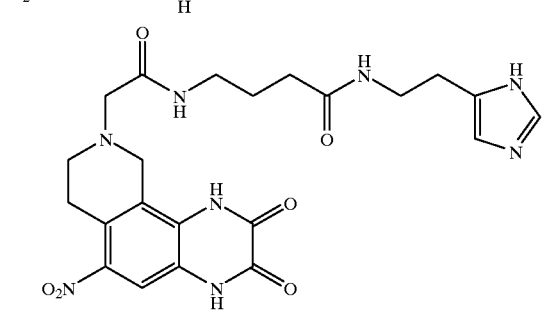

A mixture of the free acid from Example 6 (0.1 g, 0.25 mmol), histamine (31 mg, 0.275 mmol), triethylamine (70 µL), 1-ethyl-3-(3-dimethylaminopropyl)carbodiimide (EDAC) (53 mg, 0.275 mmol), hydroxybenztriazole (37 mg, 0.275 mmol) in DMF (7 mL) was stirred under a nitrogen atmosphere at 0° C. After 20 hours, additional histamine (10 mg) and triethylamine (35 µL) were added. After 3 days, the solvent was removed and the residue suspended in water and heated to boiling, and filtered while hot. The filtrate was cooled in the refrigerator overnight and the precipitate collected by filtration, washed with water and acetone, and dried in vacuo to give the product (43 mg) in 34% yield as a yellow brown solid; m/e M+1 499, IR, nmR, HPLC.

EXAMPLE 10

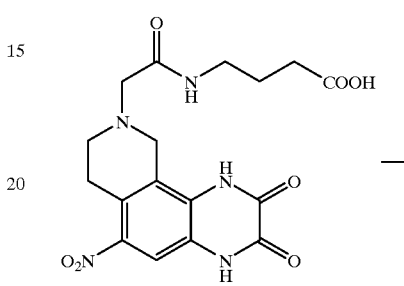

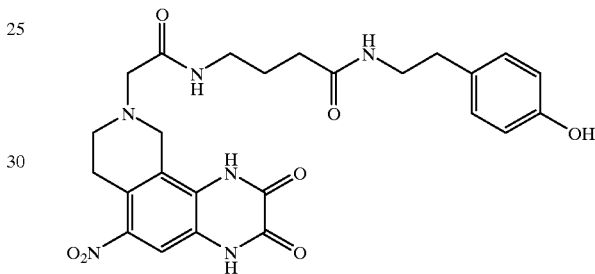

A mixture of the free acid from Example 6 (0.1 g, 0.25 mmol), triethylamine (70 µL), EDAC (53 mg, 0.275 mmol), and N-hydroxybenzotriazole (HOBT) (37 mg, 0.275 mmol) in DMF (7 mL) was stirred under a nitrogen atmosphere for 15 minutes at 0° C. and then treated with tyramine (0.04 g, 0.275 mmol). After stirring for 20 hours at room temperature, additional tyramine (10 mg) and triethylamine (35 µL) were added. After 20 hours, the solvent was removed and the residue suspended in water and sonicated for 2 h (45° C.). The insoluble material was collected by filtration, washed with diethyl ether and acetone and dried in vacuo; m/e M+1 525, nmR, HPLC.

EXAMPLE 11

9-Diethylaminoacetyl-6-nitro-1,4,7,8,9,10-hexahydro-pyrido[3,4-f]quinoxaline-2,3-dione

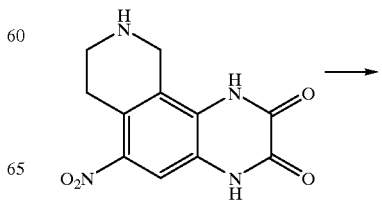

-continued

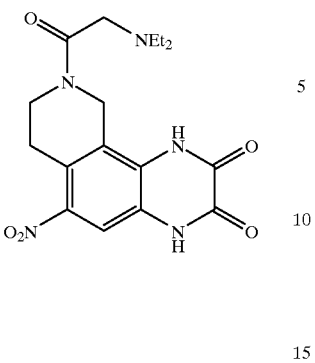

A mixture of N,N-diethylglycine hydrochloride (96 mg, 0.57 mmol) and carbonyldiimidazole (92 mg, 0.57 mmol) in THF (5 mL) were refluxed under a nitrogen atmosphere for 15 min. With the bath temperature at 70° C., DMF (7 mL) and 6-nitro-pyridoquinoxalinedione (0.1 g, 0.38 mmol) were added, and finally triethylamine (265 μL) was added and the reaction heated for 14 h at 80° C. The solvent was removed and the residue triturated with water, collected by filtration and washed with diethyl ether. An orange brown solid (104 mg) was obtained in 73% yield, mp 285–290° C. (dec); m/e M+1 376, nmR, IR.

EXAMPLE 12

9-(3-Diethylamino-propionyl)-6-nitro-1,4,7,8,9,10-hexahydro-pyrido[3,4-f]quinoxaline-2,3-dione

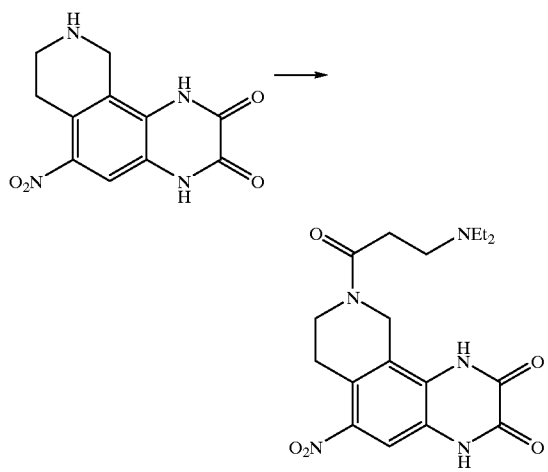

The same procedure as shown in Example 11 was employed, except N,N-diethyl-3-aminopropionic acid hydrochloride was used as substrate to give the product as an orange brown solid (104 mg); mp=240–245° C. (dec), IR, nmR.

EXAMPLE 13

9-(4-Dimethylamino-butyryl)-6-nitro-1,4,7,8,9,10-hexahydro-pyrido[3,4-f]quinoxaline-2,3-dione

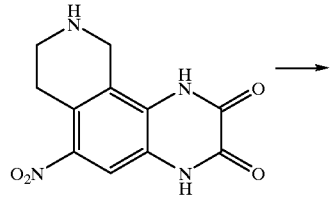
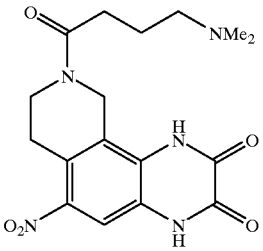

The same procedure as shown in Example 11 was employed, except N,N-dimethyl-4-aminobutyric acid hydrochloride was used as substrate to give the produce as a yellow solid (104 m); mp=295–300° C. (dec), m/e M+1 376, IR, nmR.

EXAMPLE 14

6-Nitro-2,3-dioxo-1,2,3,4,7,10-hexahydro-8H-pyrido[3,4-f]quinoxaline-9-carboxylic Acid Diethylamide

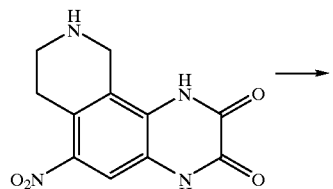

The same procedure as shown in Example 11 was employed, except diethylcarbamyl chloride (0.46 mmol) was used as substrate to give the product as a beige solid (104 mg); mp=>300° C., m/e M+1 362, IR, nmR.

EXAMPLE 15

6-Nitro2,3-dioxo-1,2,3,4,7,10-hexahydro-8H-pyrido[3,4-f]quinoxaline-9-carbothioic Acid Phenylamide

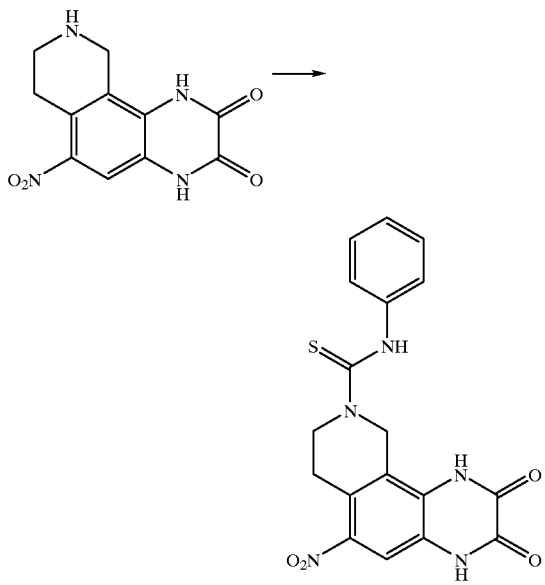

A mixture of the 6-nitropyridoquinoxalinedione (0.1 g, 0.38 mmol), phenylisothiocyanate (70 μL), triethylamine (70 μL) in DMF (5 mL) was stirred at 60° C. for 24 hours. The mixture was poured onto water and allowed to stand. The precipitate was collected by filtration, washed with water and ether, and dried in vacuo to give product (130 mg) as a beige solid; mp 270–274° C., nmR, IR.

EXAMPLE 16

6-Nitro-9-(thiophene-2-sulfonyl)-1,4,7,8,9,10-hexahydro-pyrido[3,4-f]quinoxaline-2,3-dione

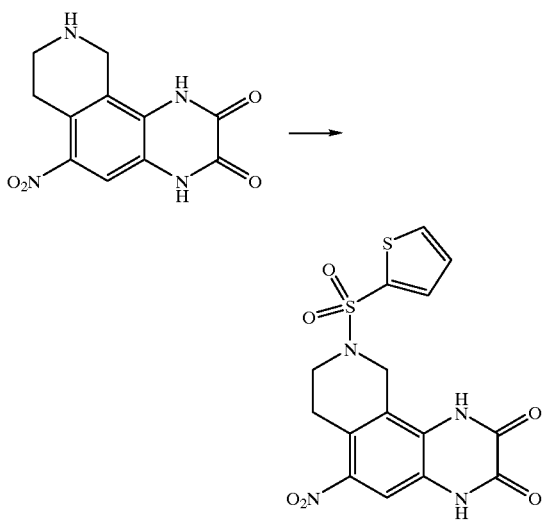

A mixture of the 6-nitropyridoquinoxalinedione (0.1 g, 0.38 mmol), 2-chlorosulfonyl thiophene (104 mg, 0.57 mmol), triethylamine (70 μl) in THF (5 mL) and DMF (5 mL) was stirred at 60° C. for 24 hours. The mixture was poured onto water and diethyl ether. The precipitate was collected by filtration, washed with water and ether, and dried in vacuo to give product as a yellow solid (80 mg) in 52% yield; mp >300° C. m/e, M+1 409 nmR, IR, CHN.

EXAMPLE 17

9-(1-Methyl-1H-imidazole-4-sulfonyl)-6-nitro-1,4,7,8,9,10-hexahydro-pyrido[3,4-f]quinoxaline-2,3-dione

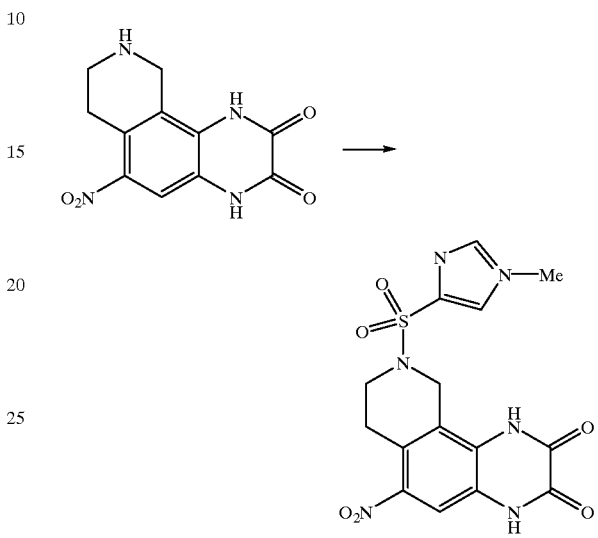

The product was obtained in an identical manner as Example 16 except that 1-methyl-1H-imidazole-4-sulfonylchloride was used as the substrate to give the product as a yellow solid (100 mg); mp 235–240° C., m/e M+1 407, IR, nmR.

EXAMPLE 18

Preparation of PNQX Antisera

The compound prepared in Example 5 (4-[2-(6-nitro-1,2,3-dioxo-1,2,3,4,7,10-hexahydro-8H-pyrido[3,4-f]quinoxaline-9yl)-acetylamino]-butyric acid) (50 mg, 123 nmol), and porcine thyroglobulin, pTG (50 mg, 75 nmol) were dissolved in water (5 mL). 1-Ethyl-3-(3-dimethylaminopropyl)-carbodiimide (100 mg, 525 nmol) was slowly added and the reaction stirred at room temperature in the dark for 48 hours. The mixture was dialyzed 5 times for 24 hours against 4 L of 0.9% NaCl. The resulting solution with an approximate ratio of 30 to 50 moles PNQX analog per mole pTG was diluted to 3 mg/mL protein and stored at 4° C. until used. The PNQX-pTG conjugate was used to immunize female New Zealand white rabbits (500 μg conjugate per animal per immunization in Freund's complete adjuvant). This was allowed by booster immunizations at two week intervals with 500 μg of conjugate in Freunds incomplete adjuvant. After two to three immunizations the animals were bled, the antisera collected and the titer of the antisera determined by measuring the amount of radiolabel bound at increasing dilutions of antisera. For use in the enzymatic immunoassay, the antibody (anti-PNQX-IgG) was purified from the antisera by protein A affinity chromatography.

EXAMPLE 19

Preparation of Radioiodinated PNQX Analog

A radioiodinated label was prepared by adding the compound of Example 10 (5 μg, 9.5 nmol) to $Na^{125}I$ (1.0 mCi)

in 40 μL of 0.5M potassium phosphate buffer, pH 7.4. Reaction was initiated with the addition of chloramine-T (30 mg, 160 nmol), mixed at room temperature for one minute, then quenched by the addition of sodium metabisulfate (10 μg, 53 nmol). The radiolabeled product was purified by high pressure liquid chromatography using an C-18 reversed phase analytical column available from Alltech Co., Deerfield, Ill. and employing a gradient of acetonitrile in 0.05M potassium formate at pH 4.0. The radiolabeled fraction was diluted in 0.01M sodium phosphate buffer containing 0.14M NaCl, 0.01% thimerosal and 0.1% swine skin gelatin at a pH of 7.4 to 50,000 counts per minute (cpm) for use in the radio immunoassay.

EXAMPLE 20

The radioimmunoassay of this invention was used to determine the uncorrected free concentration of PNQX in brain interstitial fluid following a neuroprotective dose of PNQX to rats and to determine the effect of probenecid on PNQX plasma and brain interstitial fluid concentrations. Guide cannulas were stereotaxically positions in striatum 3 days prior to the study. Microdialysis probes were inserted in guide cannulas in the rats 2 hours prior to PNQX administration. The probes where perfused with artificial CSF (buffer containing: $Na^+$, 141 mM; $K^+$, 3.3 mM; $Ca^{+2}$, 1.25 mM; $mg^{+2}$, 1.2 mM; $Cl^-$, 152 mM; $HPO_4^{-2}$, 0.48 mM; $HCO_3^-$, 21 mM; glucose 3.4 mM; urea, 2.2 mM at pH 7.40) at 2 μL/min. All the rats (N=4) received a 4-hour infusion of PNQX at a rate of 2.5 mg/kg/hr, a neuroprotective dose in focal, reperfusion ischemia. In two of four rats, probeneacid was coadministered at a rate of 200 mg/kg bolus loading doses and 50 mg/kg/hr maintenance dose for 4 hours. The PNQX concentration was measured in the brain dialysate samples using the radioimmunoassay of this invention which provided a lower limit of quantitation of 40 pg/mL in the dialysate.

The assay is based on the ability of unlabeled PNQX or crossreacting metabolites to compete with $^{125}I$ labeled PNQX analog for antibody bonding sites. On hundred microliters of standard or 20 μL of unknown or quality control samples were allowed to incubate with constant amounts of antibody and radiolabel for 2.5 hours at 23° C. The antibody-radiolabel complex was then precipitated with sheep anti-rabbit gamma globulin antibody. Following decanting of the supernatant, the precipitate was counted in a Packard Cobra gamma counter (Packard Instrument Co., Downers Grove, Ill.). Standard curves were generated by plotting the logit of the percent bound versus log of PNQX standard concentration using Packard Cobra data reduction software. Quality control and unknown sample concentrations were then obtained from the standard curve.

The assay found an apparent steady-state plasma concentration of PNQX was attained in both groups. The average PNQX plasma concentration after 180 minutes was 540 ng/mL in the rats treated only with PNQX while the rats treated with probenecid exhibited a PNQX concentration of about 2900 ng/mL.

The assay results for brain interstitial fluid were uncorrected for probe recovery and therefore are expected to be lower than the actual concentrations. The assay found that PNQX concentration increased in brain interstitial fluid in parallel with plasma concentration and the attained steady state. The PNQX concentration in brain interstitial fluid at 180 minutes was 1.6 ng/mL in untreated animals and 13.4 ng/mL in the probenecid treated animals.

Other variations and modifications of this invention will be obvious to those of ordinary skill in this art. This invention is not to be limited except as set forth in the following claims.

We claim:

1. A fused-azacyclic quinoxalinedione compound represented by the Formula (I):

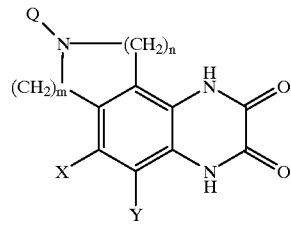

or a pharmaceutically acceptable salt thereof wherein:

X and Y are independently hydrogen, halogen, nitro, cyano, —$CF_3$, —COOH, $CONR^1R^2$, $SONR^1R^2$, $COR_3$, $SO_2R^3$, alkyl, alkenyl, imidazolyl or imidazolidinyl, wherein:

$R^1$ and $R^2$ are independently hydrogen, alkyl having 1 to 6 carbon atoms, cycloalkyl, or aralkyl and wherein:

$R^3$ is alkyl, haloalkyl, cycloalkyl, aryl or aralkyl;

Q is —$CO(CH_2)_pNR^4R^5$, —$CSNR^6$aryl, —COimidazolyl, —COthiophenyl, —$SO_2$imidazoly, —$SO_2$thiophenyl, —$(CH_2)_rCO(CH_2)_pCOOR^7$, —$(CH_2)_rCONR^4R^5$, —$(CH_2)_rCONH(CH_2)_sCONR^4R^5$, —$(CH_2)_rCONH(CH_2)_sCOOR^7$—$(CH_2)_rCONH(CH_2)_sCONHNHCO(CH_2)_vNHCOR^9$, —$(CH_2)_rCONHNHCO(CH_2)_sNHCOR^9$ or $(CH_2)_rCN$ wherein:

$R^4$, $R^5$, $R^6$, and $R^7$ are independently hydrogen, alkyl having 1 to 6 carbon atoms, aryl having 6 to 20 carbon atoms, aralkyl having 7 to 20 carbon atoms, alkylene$COOR^8$, or alkylene imidazolyl or alkylene thiophenyl any of which may be substituted by one or more of alkyl, halo, hydroxy or $^{125}I$ groups, wherein $R^8$ is hydrogen, alkyl, aralkyl or aryl, wherein $R^9$ is

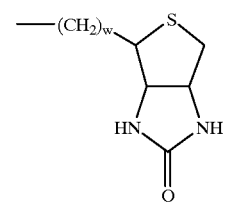

and wherein p, r, s, and w are independently 1 to 6; and m and n are independently 0, 1 or 2 provided that m+n is >1.

2. A compound according to claim 1, wherein X and Y are independently hydrogen, bromo or nitro.

3. A compound according to claim 2, wherein the fused-azacylic is a five or six member ring.

4. A compound according to claim 3, wherein Q is selected from the group consisting of

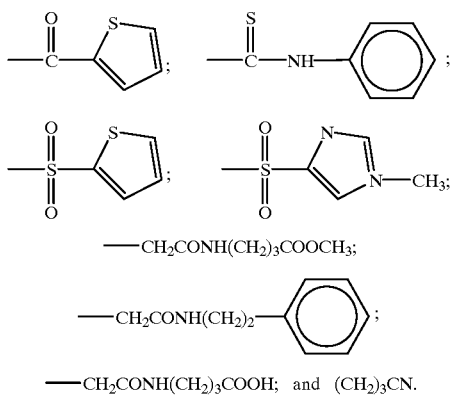

—CH₂CONH(CH₂)₃COOCH₃;

—CH₂CONH(CH₂)₂—⟨phenyl⟩;

—CH₂CONH(CH₂)₃COOH;  and  (CH₂)₃CN.

5. A compound according to claim 3, wherein Q is —CH₂CONHR', and wherein R' is selected from the group consisting of

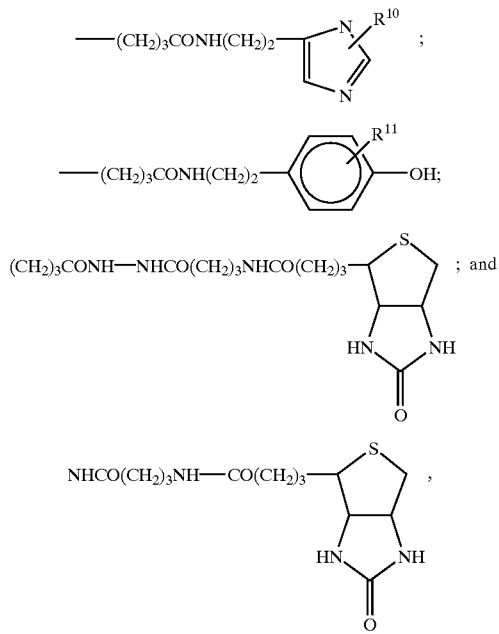

wherein $R^{10}$ and $R^{11}$ are selected from hydrogen or $^{125}I$.

6. A compound selected from the group consisting of:

9-Diethylaminoacetyl-6-nitro-1,4,7,8,9,10-hexahydro-pyrido[3,4-f]quinoxaline-2,3-dione;

9-(4-Dimethylamino-butyryl)-6-nitro-1,4,7,8,9,10-hexahydro-pyrido[3,4-f]quinoxaline-2,3-dione;

9-(3-Diethylamino-propionyl)-6-nitro-1,4,7,8,9,10-hexahydro-pyrido[3,4-f]quinoxaline-2,3-dione;

6-Nitro-2,3-dioxo-1,2,3,4,7,10-hexahydro-8H-pyrido[3,4-f]quinoxaline-9-carbothioic acid phenylamide;

6-Nitro-9-[2-(2H-tetrazol-5-yl)-benzoyl]-1,4,7,8,9,10-hexahydro-pyrido[3,4-f]quinoxaline-2,3-dione;

6-Nitro-9-(thiophene-2-sulfonyl)-1,4,7,8,9,10-hexahydro-pyrido[3,4-f]quinoxaline-2,3-dione;

9-(1-Methyl-1H-imidazole-4-sulfonyl)-6-nitro-1,4,7,8,9,10-hexahydro-pyrido[3,4-f]quinoxaline-2,3-dione;

4-[2-(6-Nitro-2,3-dioxo-1,2,3,4,7,10-hexahydro-8H-pyrido[3,4-f]quinoxaline-9yl)-acetylamino]butyric acid methyl ester;

2-(6-Nitro-2,3-dioxo-1,2,3,4,7,10-hexahydro-8H-pyrido[3,4-f]quinoxaline-9-yl)-N-phenethyl-acetamide;

4-(6-Nitro-2,3-dioxo-1,2,3,4,7,10-hexahydro-8H-pyrido[3,4-f]quinoxaline-9-yl)-butyronitrile; and 4-[2-(6-Nitro-1,2,3-dioxo-1,2,3,4,7,10-hexahydro-8H-pyrido[3,4-f]quinoxaline-9-yl)-acetylamino]-butyric acid.

7. A pharmaceutical composition useful for treating disorders responsive to the blockade of aspartate, glutamate or kainate receptors selected from epilepsy, anxiety, schizophrenia, depression, neuropathic pain, central nervous systems degenerative disorders, cerebral hapax/ischemic conditions or stress related psychiatric disorders, said composition comprising a pharmaceutically acceptable carrier or diluent and a therapeutically effective amount of at least one compound of claim 1.

8. A method for treating anxiety in a human suffering thereof which comprises administering an effective amount of at least one compound of claim 1.

9. A method for treating cerebral hapax ischemia in a human suffering thereof which comprises administering an effective amount of at least one compound of claim 1.

* * * * *

UNITED STATES PATENT AND TRADEMARK OFFICE
CERTIFICATE OF CORRECTION

PATENT NO. : 5,968,928
DATED : Oct. 19, 1999
INVENTOR(S) : Bigge et al.

It is certified that error appears in the above-identified patent and that said Letters Patent is hereby corrected as shown below:

Column 24, line 22, "COR$_3$" should read "COR$^3$".

Column 24, line 31
" -SO$_2$imidazoly, " should read
" -SO$_2$imidazolyl, ".

Column 24, lines 33-34
" -(CH$_{2r}$CONH(CH$_{2s}$CONR$^4$R$^5$, -(CH$_{2r}$CONH(CH$_{2s}$COOR$^7$ " should read
" -(CH$_2$)$_r$CONH(CH$_2$)$_s$CONR$^4$R$^5$, -(CH$_2$)$_r$CONH(CH$_2$)$_s$COOR$^7$, ".

Column 24, line 36, "(CH$_{2r}$CN" should read "(CH$_2$)$_r$CN".

Column 25, the two structures at lines 30-45, insert a hyphen before "(CH$_2$)$_3$CONH..." and "NHCO(CH$_2$)$_3$NH...".

Column 26, lines 42 and 46, in each instance, insert -- in unit dosage form -- after "1".

Signed and Sealed this

Sixteenth Day of May, 2000

*Attest:*

*Attesting Officer*

Q. TODD DICKINSON

*Director of Patents and Trademarks*